United States Patent [19]
Updyke et al.

[11] Patent Number: 5,775,913
[45] Date of Patent: Jul. 7, 1998

[54] PROCESS FOR MINIMAL TIME TOOTH CAPPING

[76] Inventors: John R. Updyke, 11923 Brookwood Cir., Austin, Tex. 78750; Robert D. Martin, 4409 Malaga Dr., Austin, Tex. 78759; David G. Lippincott, 12021 Ladrida La., Austin, Tex. 78727

[21] Appl. No.: 863,178

[22] Filed: May 27, 1997

[51] Int. Cl.$^6$ .................................................. A61C 5/02
[52] U.S. Cl. ........................ 433/223; 433/34; 264/16
[58] Field of Search ................... 433/34, 223; 264/16, 264/19; 249/54; 425/DIG. 11

[56] References Cited

U.S. PATENT DOCUMENTS

| | | | |
|---|---|---|---|
| 503,826 | 8/1893 | Brewster | 249/54 |
| 4,411,625 | 10/1983 | Koblitz et al. | 433/217.1 |
| 4,504,230 | 3/1985 | Patch | 433/219 |
| 4,678,435 | 7/1987 | Long | 433/218 |
| 5,192,207 | 3/1993 | Rosselini | 433/223 |
| 5,332,390 | 7/1994 | Rosellini | 433/34 |
| 5,368,481 | 11/1994 | Hill | 433/34 |

*Primary Examiner*—John J. Wilson
*Attorney, Agent, or Firm*—Joseph F. Long

[57] ABSTRACT

A method for making caps of eight different sizes for each of a persons teeth allows premaking caps that will fit almost any tooth of any patient; caps are preferably prepared from a commercially available quartz or silicon dioxide filled acrylic material called Artglass (r); the caps allow curing a material such as Charisma (r) with ultraviolet light thereby allowing a practitioner to place a cap containing Charisma (r) over a tooth prepared for capping; settle the cap in place; remove any excess and expose the capped tooth with a ultraviolet light for about three minutes to form a solidly capped tooth in one visit to the practitioners office.

2 Claims, 3 Drawing Sheets

PROCESS FOR MINIMAL TIME TOOTH CAPPING

BACKGROUND OF THE INVENTION

Huge strides have been made in the field of dentistry and tooth care since George Washington reportedly used wooden pegs for a tooth replacement. Currently capping or putting crowns on teeth require the dentist to grind the tooth to remove decay and to grind to a relatively small flat top pyramid shape to receive a made to-order crown. A temporary material is then used to protect the tooth for the two or more days usually required to make the needed new crown or cap.

This invention addresses the problem as outlined and provides the dentist with a way to cap a tooth with a single visit to the dentist's office. Filled, light polymerizable plastics with special properties to simulate or improve on properties of a natural tooth make this improvement possible. The presently preferred material for the outer shell or cap is known as ARTGLASS (r) developed in 1995. Artglass (r) is available from Heraeus Kulzer Inc.Co..Dental Lab Division, Muirlands Blvd., Irvine, Calif. 92618-2595. ARTGLASS (r) is a light polymerizable multifunctional methacrylate monomer capable of forming a highly crosslinked three dimensional molecular network and filled with about 20% glass particles of about a two micrometer size and about 55% of glass particles of about seven tenths micrometer size. With filling of this size the surface is sufficiently smooth as to have a lustrous appearance. When light cured or polymerized the cured material is harder, has more fracture resistance. and is more abrasion resistant than any of the ceramics or hybrid composites normally used for crowns or bridges. The preferred light polymerizable material for use inside the cap when the cap is fabricated from ARTGLASS r is Charisma r. The Charisma (r), also available from Hereaeous Kulzer Inc.,Co., is ultraviolet light curable inside the mouth in about three minutes. Charisma (r) is comprised of a multifunctional methacrylate monomer capable of forming a highly crosslinked three dimensional molecular network and filled with about 75% of glass particles of about seven tenths micrometer size. The properties of the cured Charisma (r) are essentially the same as the Artglass (r).

Tooth sizes vary in people but caps of about eight sizes for each tooth would allow capping of essentially all the teeth in the populace.

Using a three piece glass or methacrylate polymer mold ARTGLASS (r) can be molded and light cured to form a cap approximately twenty five thousandths of an inch thick. With much less grinding than necessary for the presently used procedure a cap of one of the eight sizes will loosely fit over the tooth. The lesser grinding required is a special advantage in capping of childrens' teeth since in a child the nerve cavity is at a maximum size, leaving a lesser portion of the tooth that may be ground off to receive a normal cap. With a small amount of the uncured Charisma r placed in the cap the cap may be placed over the tooth and the cap may be settled in place by the patient biting down. The dentist may then remove any excess material forced out and using the light source cure the interior material to bond with the tooth and become integral with the cap or crown.

The dentist may do minor grinding to get a perfect comfortable fit and may grind through the cap since the cap and Charisma (r) put in the cap have essentially the same cured properties. The Artglass (r) that forms the cap may be colored to match a patients tooth and Charisma (r) put in the cap may be also be colored to closely match the patients tooth since the cap is translucent.

Molds for forming the caps of the polymerizable material such as Artglass (r) or similar material may be formed in glass or in a plastic that is transparent to the ultraviolet light that is necessary to cure the polymerizable material.

The closest prior art that we have found is U.S. Pat. No. 5,192,207 dated Mar. 9, 1993, entitled "Composite Resin Crown, Replacement Tooth and Method" issued to Rosellini and U.S. Pat. No. 5,332,390 issued Jul. 26, 1994 entitled "Shell Tooth Form" also issued to Rosellini. Our invention differs significantly in that:

- our shell is quartz or silicon dioxide filled to give wearability equivalent to porcelain whereas the transparent shell specified by Rosellini could not be filled with quartz or silicon dioxide and quite likely does not have equivalent wearability. A filling material to allow transparency would necessarily have the same refractive index as the polymerized polymer. Our preferred Artglass (r) material is filled with quartz particles of less than two micrometers in cross section and is translucent and has wearability essentially equal to porcelain. Our translucent cap will pass sufficient ultraviolet light to cure the Charisma (r) cap filler recommended in about three minutes curing time;
- with our invention grinding through the prepared cap is of little consequence since ultraviolet light cured Charisma (r) has wear properties similar to tooth enamel;
- in our system caps for eight sizes of each tooth are compression molded giving caps that will fit almost any tooth;
- our system differs from Rossellini in that our caps may be colored to match a patients teeth;
- our system is similar to Rosellini in that the Charisma (r) filling material may be colored to match existing teeth.

SUMMARY OF THE INVENTION

The invention encompasses making caps of eight different sizes for each tooth in a patients mouth. With eight sizes available for each tooth there will be a cap to fit almost any patients tooth. Caps are made of Artglass (r), an acrylic plastic material filled with essentially round quartz particles of less than two micrometers in size and that when specially cured in an oven with a narrow ultraviolet light wavelength band has almost ideal properties for dental use and is translucent and allows normal ultraviolet light to pass through. Thus a practitioner may partially fill an Artglass (r) cap with an ultraviolet light curable material such as Charisma (r); place this over a tooth prepared for capping, settle the cap in place by having the patient bite down, remove excess material and using ultraviolet light for about three minutes cure the Charisma (r) in place in the mouth to form a solidly capped tooth.

DETAILED DESCRIPTION OF THE INVENTION

Figure 1:
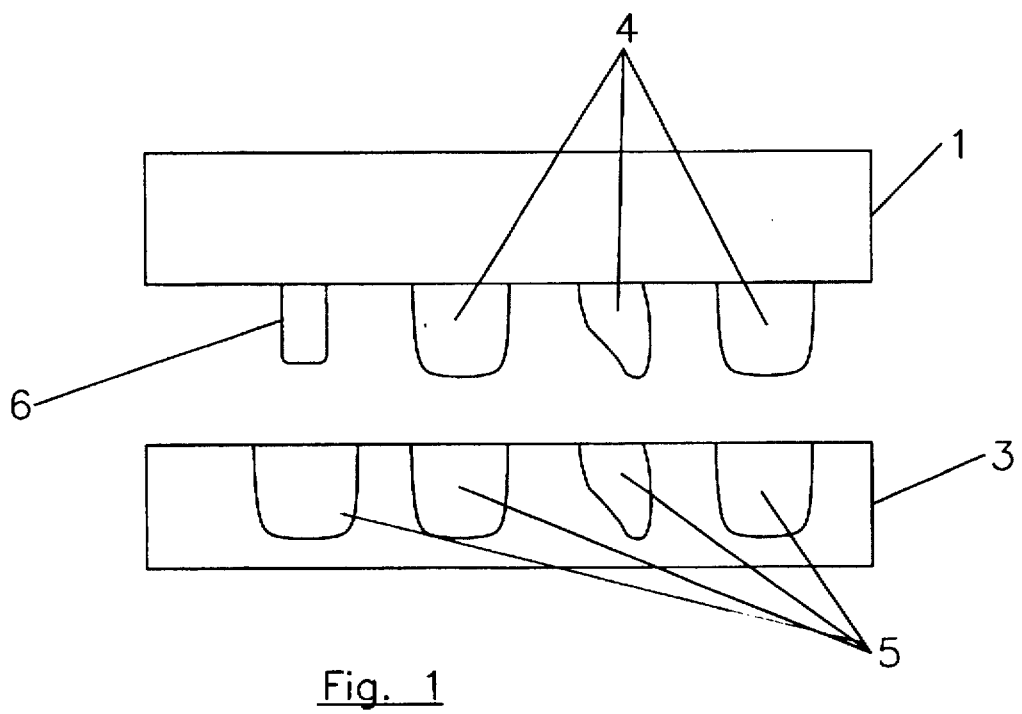
FIG. 1 shows a compression mold for formation of various tooth caps or crowns.

In FIG. 1 simple equipment for small volume formation or molding of caps is shown. Both the upper mold plate 1 and the split lower mold plate 3 are fabricated of material transparent to ultraviolet light such as glass or acrylate polymers since at present the commercially available material with the most desirable properties for this type of dental use is polymerizable or curable by use of ultraviolet light. In plate 1 male molds 4 are shown that may be precisely guided into female molds 5 in plate 3 with about twenty five thousandths of an inch clearance in order to form a cap with about a twenty five thousandths of an inch sidewall. Male mold 6 on plate 1 is about fifty thousandths of an inch larger than the metal post normally used for a jaw mounted replacement tooth. Female molds 5 may be sculptured to form a replacement tooth of any size and shape desired. The dentist may do minor necessary shaping to give exact match and fit for the replacement tooth.

Figure 2:
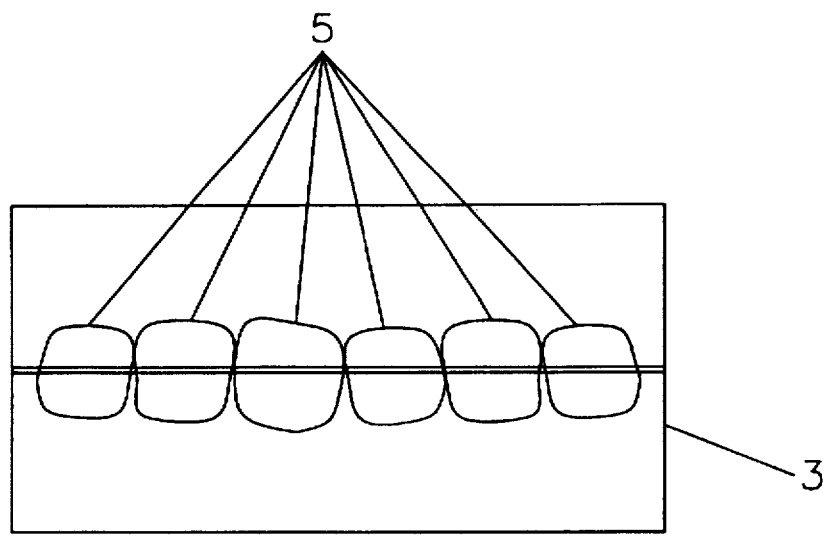
FIG. 2 shows the bottom of a three part mold that is necessary to mold a cap of the proper shape.

FIG. 2 shows the female mold 3 split in the middle to allow removal of a properly shaped tooth cap that is normally larger at the top than at the bottom. No.'s 5 are tops of molds for differing size teeth.

Figure 3:
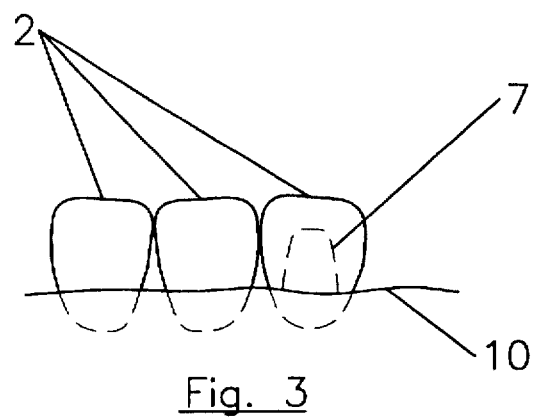
FIG. 3 indicates grinding on a tooth that is necessary for a normal type crown.

In FIG. 3 shape of normal teeth 2 are indicated as shown projecting below the gum line 10 with a dotted line 7 indicating the amount of tooth that must be ground away in order to put the normal crown or cap on the tooth.

Figure 4:
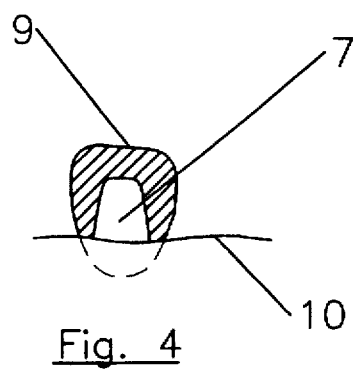
FIG. 4 indicates necessary size of normal crown or cap.

In FIG. 4 a crown 9 is shown fitted over the tooth stub 7 after crown 9 has been formed to the exact shape of the previously existing tooth. This manufacture takes some two or three days while the patient is fitted with some uncomfortable temporary crown. The bulky shape of the crown 9 is necessary to get sufficient strength for normal use.

Figure 5:
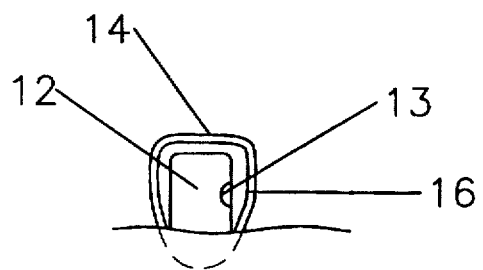
FIG. 5 indicates the reduced grinding necessary using the system of this invention.

FIG. 5 shows the thinner cap of our invention with the lesser grinding to prepare tooth 12 with area 13 indicating a spot where decay has been removed. This spot would be filled by material 16 such as Charisma (r) and cured to become an integral part of the cap 14.

Figure 6:
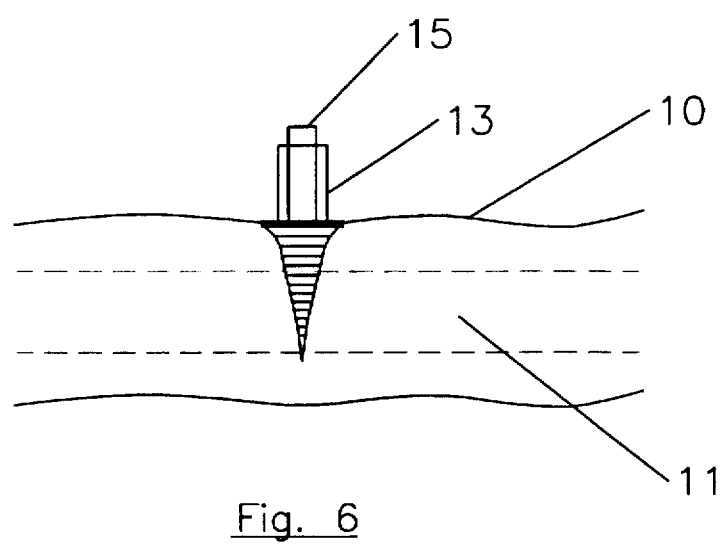
FIG. 6 indicates base of replacement tooth.

FIG. 6 shows a tooth replacement pivot 13 that is fastened to the jawbone 11 with post 15 that is normally metal. In our system a fully formed tooth as indicated in one of the mold forms in FIG. 1 may be slipped over post 15 and with a very small amount of material such as indicated in 16, FIG. 5 integrally held in place.

Figure 7:
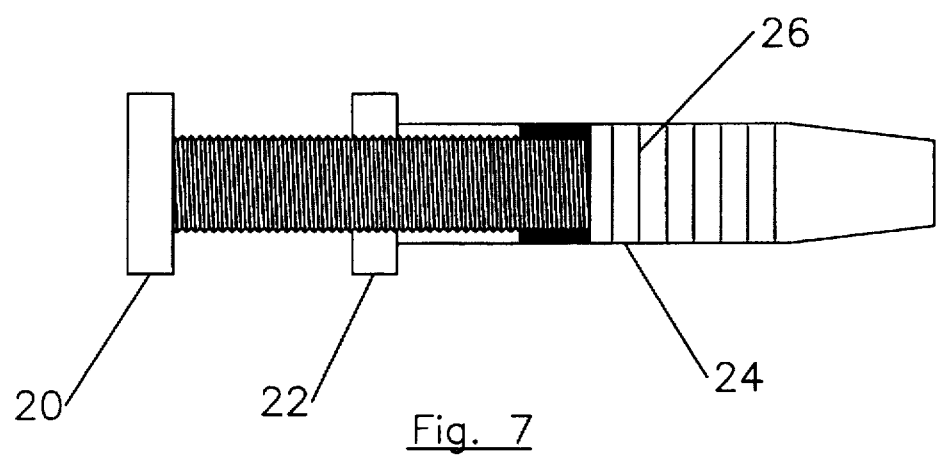
FIG. 7 shows a type of polymer measuring device to aid in properly filling the cap molds.

FIG. 7 shows a measuring and dispensing unit 24 to measure the unpolymerized material to make caps or put into cap interiors as discussed. Plunger 20 is threaded through cap 22 since the filled unpolymerized material is quite viscous. Calibration marks 26 are used to indicate the amount of material expressed.

What is claimed is

1. A method for forming a tooth cap comprising:

A) forming multiple female molds forms in a first split ultraviolet light transparent lower mold base;

B) forming multiple male mold forms in a second ultraviolet transparent upper mold base; said male mold forms being about twenty five thousandths of an inch smaller than said female mold forms and being in the same shape and being located to be precisely guided into said female mold forms;

C) pressuring said female mold form split bases to-gether and placing an amount a multifunctional methacrylate monomer capable of forming a highly crosslinked three dimensional molecular network and filled with about 20% glass particles of about a two micrometer size and 55% of glass particles of about seven tenths micrometer size in each of said female mold forms to fill a space between said male mold form and said female mold forms;

D) pressuring said second ultraviolet transparent upper mold base against said first split ultraviolet transparent lower mold base;

E) exposing said molds in said upper and lower mold bases to ultraviolet light to polymerize said multifunctional methacrylate monomer and F) removing said caps from said mold forms.

2. A method for capping a patients tooth comprising:

A) measuring a length and width of each side of said tooth to be capped;

B) choosing a cap prepared from a multifunctional methacrylate monomer capable of forming a highly crosslinked three dimensional molecular network and filled with about 20% glass particles of about a two micrometer size and 55% of glass particles of about seven tenths micrometer size from a group of previously prepared caps of approximately the same size as said tooth to be capped;

C) grinding said tooth to be capped to allow said chosen cap to fit over said tooth;

D) choosing a portion of a multifunctional methacrylate monomer capable of forming a highly crosslinked three dimensional molecular network and filled with about 75% of glass particles of about seven tenths micrometer size—that has a color similar to a color of said patients teeth;

E) placing a quantity of said multifunctional methacrylate monomer capable of forming a highly crosslinked three dimensional molecular network and filled with about 75% of glass particles of about seven tenths micrometer size inside said chosen cap and placing said cap over said tooth to be capped and having said patient bite to settle said cap in place and removing any excess of said chosen material;

F) exposing said capped tooth to ultraviolet light for a minimum of approximately three minutes; and G) grinding and polishing said capped tooth to attain a comfortable fit for said patient.

* * * * *